United States Patent [19]

Lamendola et al.

[11] Patent Number: 4,831,193

[45] Date of Patent: May 16, 1989

[54] SYNTHESIS OF 3-AMINO-2-METHYLBENZOTRIFLUORIDE

[75] Inventors: Joseph F. Lamendola, Lawrenceville; Dhiru Vashi, Princeton Junction, both of N.J.; Robert G. Tyson, Prestatyn, Wales

[73] Assignee: Schering Corporation, Kenilworth, N.J.

[21] Appl. No.: 64,891

[22] Filed: Jun. 19, 1987

[51] Int. Cl.$^4$ .................... C07C 85/11; C07C 79/10
[52] U.S. Cl. ................................. 564/417; 564/416; 564/419; 568/936; 568/939; 568/940; 585/446
[58] Field of Search ............... 568/936, 939, 940; 564/416, 417, 419; 585/446

[56] References Cited

U.S. PATENT DOCUMENTS

| 2,012,985 | 9/1935 | Castner | 260/142 |
| 4,081,554 | 3/1978 | Cragoe, Jr. et al. | 424/317 |
| 4,132,737 | 1/1974 | Molloy | 260/578 |

Primary Examiner—Richard L. Raymond
Assistant Examiner—Peter G. O'Sullivan
Attorney, Agent, or Firm—John J. Maitner; Stephen I. Miller; James R. Nelson

[57] ABSTRACT

This invention relates to a novel process for preparing 3-amino-2-methylbenzotrifluoride from benzotrifluoride. The process comprises nitrating benzotrifluoride to form 3-nitrobenzotrifluoride, reacting this compound with trimethyl sulphoxonium halide to form 3-nitro-2-methylbenzotrifluoride and reducing the nitro group to an amino group.

19 Claims, No Drawings

SYNTHESIS OF 3-AMINO-2-METHYLBENZOTRIFLUORIDE

BACKGROUND OF THE INVENTION

This invention relates to a novel synthesis for the preparation of 3-amino-2-methylbenzotrifluoride. More particularly, this invention relates to a novel process wherein 3-amino-2-methylbenzotrifluoride is prepared from relatively inexpensive and readily available reactants under conditions which are essentially non-hazardous.

The compound 3-amino-2-methylbenzotrifluoride, is a valuable intermediate in the preparation of therapeutic agents. For example, U.S. Pat. No. 3,337,750 discloses that 2(2-methyl-3-trifluoromethyl)anilino nicotinic acid is a useful therapeutic agent having valuable anti-inflammatory/analgesic properties. U.S. Pat. No. 3,390,172 discloses that N-(2-methyl-3-trifluoromethylphenyl)anthranilic acid is a valuable anti-inflammatory agent. In both instances, 3-amino-2-methylbenzotrifluoride is a essential intermediate in preparing the final therapeutic agent.

In U.S. Pat. No. 3,390,170, 3-amino-2-methylbenzotrifluoride is prepared by treating 2-methyl-2-nitrobenzoic acid with sulfur tetrafluoride at temperatures in excess of 100° C. in a stainless steel bomb for about 15 hours under higher pressure to produce 3-nitro-2-methyl-benzotrifluoride. The latter nitro compound is chemically reduced to 3-amino-2-methylbenzotrifluoride. This process presents a safety hazard in that the high pressure conditions could cause the reaction vessel to rupture, thereby releasing the corrosive reaction mixture.

U.S. Pat. No. 4,209,464 discloses a process for preparing 3-amino-2-methylbenzotrifluoride comprising (a) condensing a 3-amino-4-X-benzotrifluoride with dimethylsulfoxide in the presence of an activating agent, (b) heating the N-(2-X-5-trifluoromethylphenyl)-S,S-dimethyl sulfimide at from about 85° C. to about 200° C., and (c) chemically reducing the so-formed 3-amino-2-methylthiomethylbenzotrifluoride wherein X is hydrogen, chloro, bromo, iodo or alkylthio.

We have now discovered a method for preparing 3-amino-2-methylbenzotrifluoride which utilizes relatively inexpensive and readily available starting materials and which affords the desired product in good yield.

More specifically, this invention is the process for preparing 3-amino-2-methylbenzotrifluoride which comprises: (a) nitrating benzotrifluoride to prepare 3-nitrobenzotrifluoride, (b) reacting the latter compound with trimethyl sulphoxonium halide to afford 3-nitro-2-methylbenzotrifluoride and (c) reducing the nitro substituted compound to 3-amino-2-methylbenzotrifluoride.

The foregoing process may be depicted as follows:

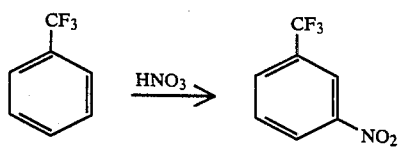

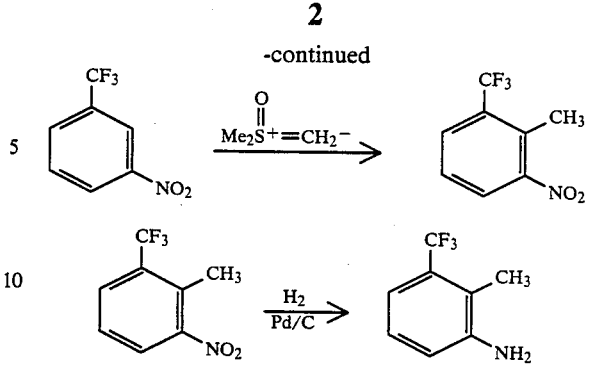

The nitration step (a) may be effected by using various nitrating agents such as concentrated nitric-sulfuric acid, potassium nitrate—sulfuric acid and nitric acid-acetic acid. The preferred nitrating agent is connected nitric-sulfuric acid. The reaction is carried out by slowly adding fuming nitric acid to a mixture of benzotrifluoride in concentrated sulfuric acid while maintaining the temperature of the reaction between 0° to 40° C., preferably 20°–30° C. When the addition is complete, the reaction is allowed to continue for 1 to 2 hours, preferably 1 hour at room temperature. 3-Nitrobenzotrifluoride is isolated from the reaction mixture by conventional techniques.

Methylation of 3-nitrobenzotrifluoride is carried out by reacting said compound with dimethyloxosulfonium methylide in a suitable aprotic solvent, e.g. dimethylsulfoxide, tetrahydrofuran and the like. The dimethyloxosulphonium methylide is derived from trimethyl sulphoxonium halide, e.g. the chloride or iodide, and a suitable base such as sodium hydride, sodium hydroxide or potassium hydroxide. The methylation reaction is carried out in an inert atmosphere, such as nitrogen, argon and the like. The reaction is carried out at a temperature below 30° C. and preferably at a temperature of about 20° C. Isolation of the desired compound is by conventional techniques.

The nitro group of 3-nitro-2-methylbenzotrifluoride is then reduced to an amino group by conventional methods well known to persons skilled in the art. In the preferred method, the nitro group is reduced by catalytic hydrogenation. Suitable catalysts include palladium on conton, or other platinum metals, and the like. Such methods are known to those skilled in the art and are described in G. W. Roberts, "Catalysis in Organic Synthesis", Academic Press, N.Y., 1976; P. H. Emmett and M. C. Yao, J.A.C.S., 81, 4125 (1959); N. Kornblum and A. Fishbein, J.A.C.S., 77, 6266 (1955); and G. B. Patent No. 832,153. The hydrogenation can be carried out by dissolving the nitro compound in an appropriate solvent such as methanol, ethanol, isopropanol and the like, in an inert atmosphere such as nitrogen, argon and the like, at room temperature. Hydrogen is passed into the solution at a temperature of from 40° C., preferably 40°–45° C. The pressure utilized during the hydrogenation is not critical, however, it is convenient to conduct the reaction at atmosphereic pressure. The reaction is run to completion which can be determined by thin-layer chromatography. The final product is isolated by conventional techniques such as filtration, distillation, etc.

The following example illustrates the process of the present invention. It will be apparent to those skilled in the art that modifications thereof may be practical without departing from the purpose and intent of this disclosure.

EXAMPLE 1

3-Amino-2-Methylbenzotrifluoride

A. 3-Nitrobenzotrifluoride

To a stirred mixture of benzotrifluoride (80.0 g, 0.55 m) and concentrated sulphuric acid (200 ml) was added fuming nitric acid (95% w/w; 29.3 ml, 44.0 g, 1.2 equivalents) over 30 minutes, maintaining the temperature of the stirred reaction mixture at between 20° and 30° by means of external cooling. After completion of the addition, stirring was continued at room temperature for a further hour and then the reaction mixture was poured onto a mixture of ice (1 kg) and water (100 ml). The resultant mixture was extracted with dichloromethane (2×250 ml) and the combined extracts washed with water (2×100 ml). The organic solution was then dried (over MgSO4) and evaporated under reduced pressure at 30° to give 3-nitrobenzotrifluoride (102 g, 94.0% w/w by GLC assay, 91% yield), as a pale-yellow oil.

B. 2-Methyl-3-Nitrobenzotrifluoride

Under an atmosphere of dry nitrogen, sodium hydride (60% w/w as a dispersion in mineral oil; 22.0 g, 0.55 m, 1.1 equivalents) was stirred with petroleum ether (b.p. 60°-80°, 100 ml) for a 5-10 minutes and then the petroleum ether was decanted. The procedure was repeated to remove all traces of mineral oil. Dimethyl sulphoxide (300 ml) was then added and the mixture heated at 70° with stirring for 30-60 minutes until all the solid had dissolved. The resultant solution was cooled to 20° and then trimethyl sulphoxonium iodide (121.0 g, 0.55 m) was added portionwise over 20-30 minutes with cooling to maintain the temperature of the stirred mixture at below 30°. Upon completion of the addition, stirring was continued at room temperature for a further 30 minutes and the resultant mixture was then added under nitrogen to a solution of 3-nitrobenzotrifluoride (95.0 g, 0.5 m) in dimethyl sulphoxide (50 ml) over 1.5-2 hours, with cooling to maintain the temperature of the reaction mixture below 30°. On completion of the addition, stirring was continued at room temperature for a further 2 hours. The reaction mixture was then diluted with water (1.5 L) and the product extracted with di-isopropyl ether (2×250 ml). The combined extracts were washed with water (100 ml) and saturated sodium chloride solution (100 ml), then dried (over MgSO4) and evaporated to give the crude product (98.0 g), as a dark-brown oil (50.5% w/w 2-methyl-3-nitrobenzotrifluoride, 36.7% w/w m-nitrobenzotrifluoride. Purification by distillation under reduced pressure gave 2-methyl-3-nitrobenzotrifluoride (32.5 g, 32% yield), as a pale-yellow oil.

C. 3-Amino-2-Methylbenzotrifluoride

A solution of 2-methyl-3-nitrobenzotrifluoride (41.0 g, 0.2 m) in methanol (100 ml) was stirred under an atmosphere of dry nitrogen at room temperature and palladium on charcoal catalyst (10% w/w, 1.0 g) was added. The stirred mixture was warmed to 40°-45° and then hydrogen was passed into the solution at atmospheric pressure until the reduction, as observed by thin-layer chromatography, was complete (4-5 hours). The solution was cooled to room temperature and the catalyst removed by filtration. Distillation of the solvent at atmospheric pressure followed by steam distillation of the crude product gave 3-amino-2-methylbenzotrifluoride (32.2 g, 92% yield), as a pale-brown oil which slowly crystallized.

We claim:

1. A process for preparing 3-amino-2-methylbenzotrifluoride which comprises the steps:
   (a) reacting benzotrifluoride with a nitrating agent to produce 3-nitrobenzotrifluoride;
   (b) reacting 3-nitrobenzotrifluoride with dimethyloxosulfonium methylide to produce 2-methyl-3-nitrobenzotrifluoride; and
   (c) reducing the nitro group in the compound of step (b) to produce 3-amino-2-methylbenzotrifluoride.

2. The process of claim 1 wherein the nitrating agent is concentrated nitric and concentrated sulfuric acid.

3. The process of claim 1 wherein the dimethyloxosulfonium methylide is derived from trimethyl sulphoxonium iodide.

4. The process of claim 1 wherein the dimethyloxosulfonium methylide is derived from trimethyl sulphoxonium chloride.

5. The process of claim 1 wherein step (b) carried out in dimethyl sulfoxide.

6. The process of claim 1 wherein the reduction in step (c) is carried out by catalytic hydrogenation.

7. The process of claim 6 wherein the catalytic hydrogenation is carried out with palladium on carbon catalyst.

8. A process for preparing 2-methyl-3-nitrobenzotrifluoride by reacting 3-nitrobenzotrifluoride with dimethyloxosulfonium methylide.

9. The process of claim 8 wherein the dimethyloxosulfonium methylide is derived from trimethyl sulphoxonium iodide.

10. The process of claim 8 wherein the dimethyloxosulfonium methylide is derived from trimethyl sulphoxonium chloride.

11. The process of claim 8 wherein the reaction is carried out in dimethyl sulfoxide.

12. The process of claim 8 wherein the reaction is carried out at a temperature below 30° C.

13. The process of claim 12 wherein the reaction is carried out at about 20° C.

14. A process for preparing 3-amino-2-methylbenzotrifluoride which comprises the steps:
   (a) reacting 3-nitrobenzotrifluoride with dimethyloxosulfonium methylide to produce 2-methyl-3-nitrobenzotrifluoride; and
   (b) reducing the nitro group in the compound of step (a) to produce 3-amino-2-methylenzotrifluoride.

15. The process of claim 14 wherein the dimethyloxosulfonium methylide is derived from trimethyl sulphoxonium iodide.

16. The process of claim 14 wherein the dimethyloxosulfonium methylide is derived from trimethyl sulphoxonium chloride.

17. The process of claim 14 wherein step (a) carried out in dimethyl sulfoxide.

18. The process of claim 14 wherein the reduction is step (b) is carried out by catalytic hydrogenation.

19. The process of claim 18 wherein the catalytic hydrogenation is carried out with palladium on carbon catalyst.

* * * * *